(12) United States Patent
Veenman

(10) Patent No.: US 12,102,082 B2
(45) Date of Patent: Oct. 1, 2024

(54) METHOD AND DEVICE FOR DISTRIBUTING A PARTICULATE MATERIAL

(71) Applicant: Koppert B.V., Berkel en Rodenrijs (NL)

(72) Inventor: Arend Veenman, Berkel en Rodenrijs (NL)

(73) Assignee: Koppert B.V., Berkel en Rodenrijs (NL)

( * ) Notice: Subject to any disclaimer, the term of this patent is extended or adjusted under 35 U.S.C. 154(b) by 26 days.

(21) Appl. No.: 16/482,920

(22) PCT Filed: Feb. 7, 2018

(86) PCT No.: PCT/NL2018/050086
§ 371 (c)(1),
(2) Date: Aug. 1, 2019

(87) PCT Pub. No.: WO2018/147733
PCT Pub. Date: Aug. 16, 2018

(65) Prior Publication Data
US 2019/0350141 A1  Nov. 21, 2019

(30) Foreign Application Priority Data

Feb. 7, 2017 (EP) .................................... 17075002

(51) Int. Cl.
*A01M 9/00* (2006.01)
*A01G 9/14* (2006.01)
(Continued)

(52) U.S. Cl.
CPC ............. *A01M 9/0007* (2013.01); *A01G 9/14* (2013.01); *A01G 13/10* (2013.01); *A01N 63/00* (2013.01);
(Continued)

(58) Field of Classification Search
CPC ............. A01M 9/0007; A01M 7/0025; A01M 9/0023; A01M 9/003; A01M 9/0046;
(Continued)

(56) References Cited

U.S. PATENT DOCUMENTS 1,873,993 A * 8/1932 Brasington ........... A01M 9/003
222/242
1,918,449 A * 7/1933 Brasington ......... A01M 9/0092
222/548
(Continued)

FOREIGN PATENT DOCUMENTS

WO  WO2007136246 A1  11/2007
WO  WO2011003078 A1  1/2011

*Primary Examiner* — Steven M Cernoch
(74) *Attorney, Agent, or Firm* — Mandar A. Josbi; Bret E. Field; Bozicevic, Field & Francis LLP

(57) ABSTRACT

The present invention relates to a method for distributing particulate material in a target area. The method comprises the steps of (i) providing in a reservoir particulate material comprising particles to be distributed in a target area, which reservoir is provided with exits, (ii) providing a gas displacer, (iii) generating with the gas displacer a forced gas flow in the blow direction, and iv) directing the particles from the exits in the forced gas flow. The invention further relates to a device for performing the method according to the invention. Further aspects of the invention relate to the use of the device for distributing particulate material, a gas flow modification device, the use of such modification device for modifying the gas flow in a device for distributing particulate material and a kit of parts comprising (a) the gas flow modification device and (b) a device for distributing particulate material.

11 Claims, 9 Drawing Sheets

(51) Int. Cl.
*A01G 13/10* (2006.01)
*A01N 63/00* (2020.01)
*B05B 3/02* (2006.01)
*B05B 5/03* (2006.01)
*B05B 5/16* (2006.01)
*B05B 7/00* (2006.01)
*A01K 67/033* (2006.01)
*A01M 7/00* (2006.01)
*A01N 63/16* (2020.01)

(52) U.S. Cl.
CPC ............... *B05B 3/02* (2013.01); *B05B 5/032* (2013.01); *B05B 5/1683* (2013.01); *B05B 7/0081* (2013.01); *A01K 67/033* (2013.01); *A01M 7/0025* (2013.01); *A01N 63/16* (2020.01)

(58) Field of Classification Search
CPC .......... A01M 9/0061; A01M 9/0069; A01M 7/0028; A01G 13/10; A01G 9/14; A01N 63/00; A01N 63/16; A01K 67/033; B05B 3/02; B05B 5/032; B05B 5/1683; B05B 7/0081; A01C 15/04
See application file for complete search history.

(56) References Cited

U.S. PATENT DOCUMENTS

| | | | | |
|---|---|---|---|---|
| 2,014,392 | A | * | 9/1935 | Mackintosh .......... A01M 9/003 43/129 |
| 4,790,484 | A | * | 12/1988 | Wall ...................... A01C 15/04 198/540 |
| 5,429,278 | A | | 7/1995 | Sansalone |
| 5,718,377 | A | | 2/1998 | Tedders et al. |
| 5,785,245 | A | * | 7/1998 | Tedders, Jr. .......... B05B 7/0861 239/9 |
| 6,491,479 | B1 | * | 12/2002 | Rexius ................... A01C 7/081 406/48 |
| 2015/0128864 | A1 | * | 5/2015 | Bolckmans ............ A01N 63/16 119/6.5 |
| 2015/0359920 | A1 | | 12/2015 | Ohtsuka et al. |

* cited by examiner

| Particle size (1) | density of particulate material | | | | |
|---|---|---|---|---|---|
| | 70-250 | 70-100 | 90-150 | 180-240 | 140-200 |
| 0.05 - 15.00 | x | x | x | x | x |
| 0.10-10.00 | x | x | x | x | x |
| 0.25-10.00 | x | x | x | x | x |
| 0.50-2.00 | x | x | x | x | x |
| 0.25-7.00 | x | x | x | x | x |

(1) Particle size in mm. Particle size is average particle size over longest axis of particles.
(2) Density of particulate material is density under standard conditions in grams per liter (g/l).
X marks a combination envisaged within the invention.

*Fig. 7*

| Length (L) of channels | DH/L | | | | | | | | |
|---|---|---|---|---|---|---|---|---|---|
| | 0.01-10 | 0.05-8 | 0.07-6 | 0.07-4 | 0.07-2 | 0.07-1 | 0.07-0.8 | 0.1-0.4 |
| 1-100 | x | x | | | | | | |
| 5-80 | x | x | x | | | | | |
| 6-70 | x | x | x | x | | | | |
| 7-60 | x | x | x | x | x | | | |
| 8-50 | x | x | x | x | x | x | | |
| 9-40 | x | x | x | x | x | x | x | |
| 10-30 | x | x | x | x | x | x | x | x |
| 10-20 | x | x | x | x | x | x | x | x |
| 10-15 | x | x | x | x | x | x | x | x |

Length (L) of channels in mm
DH/L is $D_H/L$
X marks a combination envisaged within the invention.

Fig. 8

| Area (A) of outlet | 0.01-10 | 0.05-8 | 0.07-6 | 0.07-4 | 0.07-2 | 0.07-1 | 0.07-0.8 | 0.1-0.4 |
|---|---|---|---|---|---|---|---|---|
| 10-40,000 | x | x | x | x | x | x | x | x |
| 400-6,400 | x | x | x | x | x | x | x | x |
| 400-4,900 |  | x | x | x | x | x | x | x |
| 400-3,600 |  |  | x | x | x | x | x | x |
| 900-3,600 |  |  | x | x | x | x | x | x |
| 900-2,500 | x |  |  | x | x | x | x | x |
| 900-2,000 |  |  |  |  | x | x | x | x |
| 1,200-1,800 | x |  |  |  |  | x | x | x |

Area (A) of outlets in mm
DH/L is $D_H/L$
X marks a combination envisaged within the invention.

*Fig. 9*

METHOD AND DEVICE FOR DISTRIBUTING A PARTICULATE MATERIAL

BACKGROUND

The present invention according to a first aspect relates to a method for distributing particulate material in a target area. According to a further aspect the invention relates to a device for distributing particulate material. Such a device is suitable for performing the method according to the invention. Further aspects of the invention relate to the use of the device for distributing particulate material, a gas flow modification device, the use of the gas flow modification device for modifying the gas flow in a device for distributing particulate material and a kit of parts comprising (i) the gas flow modification device and (ii) a device for distributing particulate material.

Beneficial arthropods are presently frequently used in agriculture, for example for biological pest control. Examples of beneficial arthropods, used for this purpose, are predatory mites, parasite wasps and assassin-bugs. In addition, distribution of prey, such as Astigmatid mites, for predatory arthropods, such as predatory mites, may also be beneficial in a target area where the predatory arthropods are present. This provision of (Astigmatid) prey to the predatory arthropods may help in supporting the development and maintenance of the population of predatory arthropods (see for example Hogerbrugge et al. (2008), Integrated Control in Protected Crops, Temperature Climate, IOBC/wprs Bulletin Vol 32, pp. 79-82 and EP16154905).

In order to perform their function, such beneficial arthropods must be distributed (dispersed or dispensed) in a target area, such as a crop. In the state of the art this is done by manually dispersing the beneficial arthropods (possibly on a carrier) in the crop. Alternatively predatory mites may be dispersed by using sachets, wherein an amount of such predatory mites is present. Such sachets also must be hung manually in the crop. These methods are very labour-intensive.

In order to provide a saving of labour while distributing beneficial arthropods, various devices have been designed with which such beneficial arthropods may be dispersed by means of blowing. For example WO2007/136246 discloses a method and device with which such beneficial arthropods may be dispersed by means of blowing. A device disclosed in this published international patent application is marketed by Koppert Biological Systems under the trade name Airobug™. Although the method and device disclosed in WO2007/136246 present a major advancement in the distribution of beneficial arthropods, such as predatory mites, the inventor of the present invention has found that still further improvements may be made to the method and device disclosed in this international patent application.

In particular it has surprisingly been found that the distribution of the arthropods in the axial direction (the blowing direction) is improved by using for the distribution of the arthropods a gas flow which has passed through a plurality of channels having outlets designed to direct the gas outflows (exiting the outlets of the plurality of channels) in the same direction.

In view of the fact that many of the compositions comprising beneficial arthropods, the distribution of which was at the heart of the present invention, can be considered as compositions comprising particulate material, the skilled person will understand that the various aspects of the invention described have a broader utility and may be applied more generally to the distribution of compositions comprising particulate material.

SUMMARY OF THE INVENTION

The invention thus according to a first aspect relates to a method for distributing particulate material. The method comprising:
(i) providing in a reservoir particulate material comprising particles to be distributed, which reservoir is provided with a number of exits for the particulate material;
(ii) providing a gas displacer suitable for generating a forced gas flow in a blow direction;
(iii) generating with the gas displacer a forced gas flow in the blow direction;
(iv) directing the particulate material from the exits in the forced gas flow, such that its particles are carried along in the blow direction.

The method is characterized in that a plurality of channels is provided, each channel comprising an inlet, an outlet and a hollow body connecting the inlet and outlet, wherein the inlets are designed such that at least a part of the forced gas flow flows through the channels and the outlets are designed to direct the gas outflows (exiting the outlets of the plurality of channels) in the same direction and the particles are directed from the exits in the forced gas flow after the forced gas flow has passed through the channels.

According to a further aspect the invention relates to a device for distributing particulate material comprising particles, the device comprising a reservoir suitable for holding the particles to be distributed, which reservoir is provided with a number of exits for the particles, a gas displacer suitable for generating a forced gas flow in a blow direction, which forced gas flow is suitable to carry along the particles in the blow direction, and means for directing the particles from the reservoir via the exits in the forced gas flow. This aspect of the invention is characterized in that the device comprises a plurality of channels, each channel comprising an inlet, an outlet and a hollow body connecting the inlet and outlet, wherein the inlets are designed such that at least a part of the forced gas flow, when generated, flows through the channels and the outlets are designed to direct the gas outflows (exiting from the outlets of the plurality of channels) in the same direction and the means for directing the particles from the exits in the forced gas flow are designed to direct the particles in the forced gas flow after the forced gas flow has passed through the channels. Such a device is suitable for performing the method of the invention.

Yet a further aspect of the invention relates to the use of the device of the invention in the distribution of a particulate material comprising particles in a target area, such as a crop.

A further aspect of the invention relates to the use of a gas flow modification device comprising a plurality of channels, each channel comprising an inlet, an outlet and a hollow body connecting the inlet and outlet, wherein the inlets are designed to allow a gas flow to enter the channels, such that the gas flow is able to pass through the channels, and the outlets are designed to direct the outflows of gas going through the channels in the same direction, wherein said channels are arranged together as a unit for the modification of an airflow in a particle distribution device. Such an airflow modification device is suitable for modifying and enhancing the particle distribution of a devices of the existing type as disclosed in WO2007/136246 and similar devices.

Still a further aspect of the invention relates to a kit of parts comprising the gas flow modification device and a particle distribution device of the existing type as disclosed in WO2007/136246 and similar devices.

OVERVIEW OF FIGURES

FIG. 1 provides a perspective overview of an embodiment of the particle distribution device according to the invention.

FIG. 2 provides a front view of an embodiment of a gas flow modification device of the invention.

FIG. 3 provides a side view of an embodiment of the particle distribution device according to the invention, as this is installed in a greenhouse.

FIG. 7 shows combinations of average particle size and density of particles envisaged by the invention.

FIG. 8 shows combinations of $D_H/L$ values with the length (L) of the channels envisaged by the present invention.

FIG. 9 shows combinations of the $D_H/L$ values with the area (A) of the channels envisaged by the present invention.

DETAILED DESCRIPTION OF THE INVENTION

Figure 1:
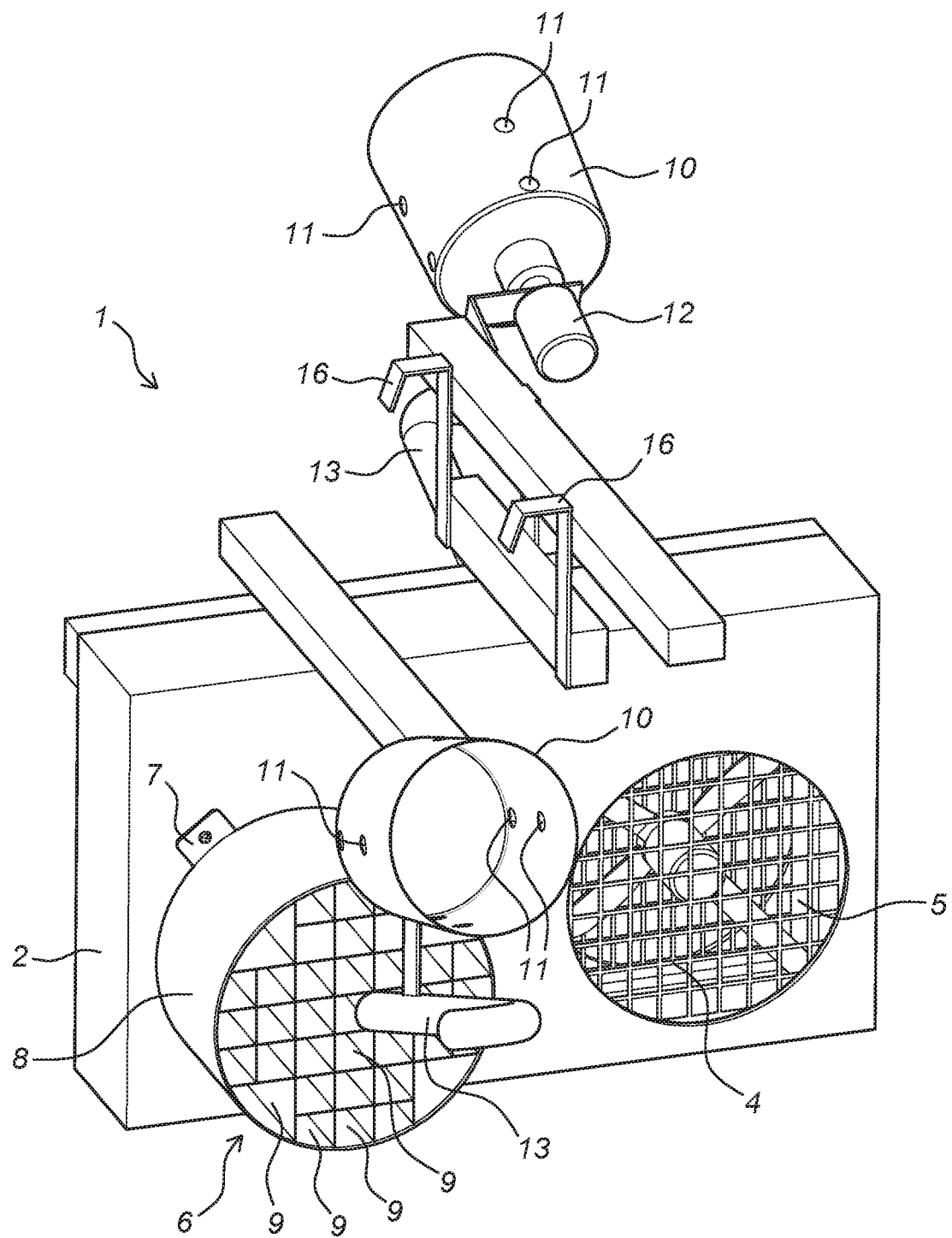

In the method according to the invention an amount of particulate material is provided in a container. As the skilled person will understand, the form and material of the container are not relevant as long as the container is suitable for holding the particulate material. The container for example is a cylindrical body, of which at least one of the circular openings is closed.

The term "particulate material" or "particulate matter" within the context of the present invention should be understood to mean a material composed of distinct particles. Particulate materials that are of particular interest, according to certain embodiments may be selected from particulate materials having applications in agriculture in particular in connection to plant health, for example as biocontrol agents or products supporting the function of biocontrol agents. In this respect it is known to the skilled person that beneficial arthropods, such as predatory mites or Astigmatid prey may be presented in compositions in combination with a carrier, such as a carrier selected from for example sawdust, wheat bran, vermiculite, or chaff, such as chaff selected from rice husks or millet chaff. Often such carriers are used in a moistened form. Such (moistened) carriers may be considered to be particulate materials. In addition individual beneficial arthropods, on an abstracted level, may also be considered to be particles. Thus a larger collection (or population) of beneficial arthropods may be considered to be a particulate material. The terms "particulate material", particulate material comprising particles" and their equivalent terms, thus within the context of the present invention includes and in particular mean "a composition comprising beneficial arthropods". "A composition comprising beneficial arthropods" may or may not comprise a suitable carrier such as mentioned above. The term "carrier" includes moistened versions. According to preferred embodiments a composition comprising beneficial arthropods does comprise a suitable carrier for the arthropod individuals.

The particles of the particulate material are suitable for distribution by blowing. The skilled person will be able to determine whether the particles of the particulate material are suitable for distribution by means of blowing. According to certain embodiments a particulate material is selected having particles with a size distribution wherein the average particle size is 0.05-15.00 mm, such as 0.10-10.00 mm, preferably 0.25-10.00 mm, such as 0.50-2.00 mm, more preferably 0.25-7.00 mm. In general such particulates will be suitable for distribution by blowing. According to some embodiments the particles have a longest axis (the particles are stretched or have a stretched shape) and the average particle size is considered over the longest axis of the particles. Examples of such particulate materials available with such an average particle size are saw dust, wheat bran, vermiculite, chaff, such as millet chaff or husks for example rice husks.

The particulate materials according to certain embodiments has a density of 50-300 grams per litre (g/l), preferably 70-250 g/l, such as 70-100 g/l, 90-150 g/l, 180-240 g/l or 140-200 g/l. Particulate materials having a density within these ranges in general can be distributed relatively easily by means of blowing. FIG. 7 shows combinations of average particle size and density of particles envisaged by the invention.

As is noted above, compositions comprising beneficial arthropods may be selected as the particulate material. The beneficial arthropods may be provided as such or in combination with a carrier. As the use of a carrier material is common for many beneficial arthropods, it should be understood that when solely the term "beneficial arthropods" or "arthropods" is used, these terms also encompass the combination with a carrier material. In connection to the present invention the term "arthropods" and "beneficial arthropods" are used interchangeably. Beneficial arthropods encompass all life stadia, inclusive eggs, nymphs (as far as these occur in a certain species), pupae (as far as these occur in a certain species), and adults of for example insects, such as parasite wasps and assassin-bugs and mites, such as predatory mites, for example phytoseiidae, such as described by De Moraes et al. (De Moraes, G. J., J. A. McMurtry, H. A. Denmark & C B. Campos (2004). A revised catalog of the mite family Phytoseiidae. Magnolia Press Auckland New Zealand). Within the term "beneficial arthropods" also other arthropods, which may be useful in biological pest control or for any other human benefit are included. When an arthropod has a suitable size and/or form and/or mass to be distributed by means of blowing (i.e. by a forced gas flow), in principle it can be distributed by using the method according to the invention. The skilled person will be able to determine whether the arthropod is suitable for distribution (dispersion) by means of blowing.

The container comprises a number of exits for the particles. Within the ambit of this invention, "a number of" comprises, each time the term is used, one or more, such as a plurality, for example 2, 3, 4, 5, 6, 7, 8, 9 or 10. The exits are suitable to allow the particles to pass. The exits are for example openings (such as holes) provided in the container. These openings may be closable by means of a closing means, such as a valve. The openings for example may be provided evenly in the mantle of a cylindrical body, of which at least one of the circular openings is closed. The openings may for example be provided on a circle on predetermined distances expressed in degrees, such as every 10-360°, for example every 45-180°, inclusive every 90°. When the axis of the cylinder is placed under an angle with the lines of gravity, the particles may be dosed by rotating the cylinder.

The dosing will amongst others depend on the size of the container, the speed of rotation, the size of the openings and the size of the particles. For example, by using these parameters the dosing of the particles may be controlled and/or influenced. Alternatively, the dosing of the particles may be controlled and/or influenced by making the opening in the container closable by means of a controllable valve and controlling the valve in agreement with the necessary dosing. The necessary dosing required to distribute sufficient in the target area, will amongst others depend on the effect of the particles required in the target area. It is within the ambit of the knowledge of the skilled person to determine the necessary dosing in the target area of the selected particles of the particulate material.

From the exit the particles are directed in a forced gas flow. With forced gas flow should be understood a gas flow which is forcefully blown and/or directed in a particular direction. The gas is preferably a gas mixture, such as air. The particles may be guided mechanically or under the influence of gravity into the forced gas flow. Suitable mechanical means will be known to the skilled person. For example, a screw transporter may be mentioned. Use of gravity is preferable. When using gravity, the exits of the particles will be placed above or in the forced gas flow.

The forced gas flow may be generated continuously or pulsating with a gas displacer. The directions wherein the forced gas flow is generated, the blow direction, may be directed horizontally, but also under an angle with the horizontal. Within the ambit of this invention a gas displacer should be understood to be a device suitable for displacing gas, for example by creating pressure differences. As a gas displacer use may be made of known means, such as for example rotors (inclusive propeller), of various designs, such as two bladed, three bladed, four bladed or other multiple bladed rotors (inclusive propellers and turbines). Alternatively, a gas container with a pressurised gas may be used as a gas displacer. When using one or more rotors these may be placed in a cylindrical rotor chamber, having an inlet and an outlet. The benefit of this is that the forced gas flow is channelled in the direction of the outlet. Relative to the gas flow generated by a rotor in free space, this gas flow is more directed in the direction of the axis of the rotor.

The method according to the invention is characterized in that a plurality of channels is provided, each channel comprising an inlet, an outlet and a hollow body connecting the inlet and outlet, wherein the inlets are designed such that at least a part of the forced gas flow flows through the channels and the outlets are designed to direct the gas outflows (exiting the outlets of the plurality of channels) in substantially the same direction or the same direction and the particles are directed from the exits in the forced gas flow after the forced gas flow has passed through the channels.

The channels may be any type of channels suitable for conveying, transporting or guiding the forced gas flow. A channel thus may be any type of duct, canal, vessel or conduit suitable for conveying, transporting and/or guiding the forced gas flow. Suitable channels may have an inlet and an outlet and a hollow body connecting the inlet and outlet. The body of a channel will have a wall, the channel wall having a channel surface in the hollow interior of the channel. In addition, the body of the channels will have an external surface having an external circumference. The inlet and outlet of a channel are positioned at a distance from each other. The skilled person will understand that such channels, as used in the invention, thus comprise a hollow body having a first opening, the inlet, connecting the interior of the hollow body with the exterior, and at a distance from the first opening a second opening, the outlet, connecting the interior of the hollow body with the exterior. The hollow body preferably is elongated.

The bodies of the channels in their cross section may have any form (or shape) suitable for conveying (or guiding) the forced gas flow. When referring to the cross section of the bodies of the channel, reference is made to the cross section of the hollow interior of the body. For example, the channels may have in cross section a rectangular form, such as a square form, a circular form, an ellipsoid form, a triangular form, or a different geometric form such as a hexagonal or pentagonal form. Alternatively, the cross section of the bodies of the channels may have an irregular form. The form of the cross section of a channel may also be different over the length of the body of the channel. It should be noted that in the present invention a plurality of channels is used and that channels used may have cross sections having different forms (or shapes). The use of channels that can be easily positioned in adjoining positions is preferred. Channels having a substantially straight configuration are beneficial in connection to this. Channels having a substantially straight or straight configuration will have a (substantially) straight (imaginary) axis. In addition, channels having an external circumference with a rectangular shape, such as a square shape, are further also beneficial in view of this. Preferably the straight configuration and rectangular shape of the external circumference are combined in selected channels.

As the skilled person will understand, the inlet and outlet will have a circumference, that corresponds to the inner surface of the hollow body at the inlet respectively the outlet. When referring to the shape or form of the inlet or outlet reference is made to the shape or form enclosed by the circumference. In general the inlet and outlet will have a form (or shape) similar to the cross section of the body of their channel. However, it is possible that the inlet and/or outlet of a channel are shaped different from the cross section of the body of their channel. A differing shape may for example result from the plane of the inlet and/or outlet not coinciding with a perpendicular section of the body of the channel, but instead coinciding with a section under an angle. The skilled person will for example understand that when a section is made under an angle in a channel having a circular cross section this will result in an ellipsoid form. The channels used thus according to some embodiments may have an inlet and/or outlet that coincide with a section of the body of the channel that has an angle (a) with a cross section of the channel. This angle (a) between the plane of the inlet and/or the outlet and the cross section of the body of the channel may for example be ≤70°, such as ≤60°, such as ≤50°, such as ≤25°, such as ≤20°, such as ≤15°, such as ≤10°, such as ≤5°, such as ≤3°, such as ≤2°, such as ≤1°. According to certain embodiments, the angle ($\alpha$) between the plane of the inlet and/or the outlet and the cross section of the body of the channel is between 0-70°, such as 0-70°, such as 0-60°, such as 0-50°, such as 0-40°, such as 0-30°, such as 0-20°, such as 0-15°, such as 0-10°, such as 0-5°, such as 0-3°. Most preferably the channels used have an inlet and outlet that coincide with a substantially perpendicular or perpendicular section of the body of the channel. The plane of the inlet and/or outlet need not be a flat plane but according to certain embodiments may be curved.

In the plane of the inlet and/or outlet and of the cross section of the body of the channel a (theoretical) centre point can be defined. On the basis of his common general knowledge, the skilled person will be able to determine the centre point of the selected inlets, outlets and cross section of the channel body. The length (L) of the channel according to certain embodiments corresponds to the length of the centre line of the channel between the centre point of the inlet and the centre point of the outlet. As the skilled person will know and understand, the centre line of a channel (or duct) is a (theoretical) line going through the centres of the total of cross sections of the channel having an infinitesimal width.

The inlet and outlet preferably are located at or near the ends of the elongated body. An inlet or outlet is considered to be located near the end of the elongated body in case the distance of the position of its centre point to the respective end of the body is less than ⅓rd, preferably less than ¼th, more preferably less than ⅕th, more preferably less than $1/10^{th}$ of the total length of the body. When the position of the centre point of the inlet or outlet is located at the end of the hollow body, the distance to the end of the hollow body will be 0, for example 0 cm or 0 mm. Such a 0 distance is also less than ⅓rd, such as less than ¼th, such as less than $⅕^{th}$, such as less than 1/10th of the total length of the body.

In case an elongated body is used wherein the inlet and outlet are located at or near the ends of the elongated body, it is preferred that the elongated body has a straight geometry or a smoothly curved form. By providing an elongated body having a straight geometry or a smoothly curved form, the chance that gas velocity and/or pressure is lost during the flow of the forced gas flow through the elongated body of the channels is reduced. The use of an elongated body having a substantially straight or straights geometry is most preferred. It is further preferred that there is a substantially straight or straight passage from the inlet to the outlet. In case the forced gas flow need not pass any corners during its passage from the inlet to the outlet, the chance that gas velocity and/or pressure is lost during the flow of the forced gas flow through the elongated body of the channels is reduced. The skilled person will understand that there is an substantially straight passage between the inlet and outlet, in case an imaginary straight line can connect the inlet and the outlet without 'cutting' the channel wall, preferably by connecting the centre point of the inlet and the centre point of the outlet. Again, by providing a substantially straight passage from the inlet to the outlet, the risk that gas velocity and/or gas pressure is lost during the passaging of the forced gas flow from the inlet to the outlet is prevented. It is preferred that the bodies of the channels are at least substantially closed such that the forced gas flow enters at the inlet and exits at the outlet and substantially does not exit elsewhere from the body of a channel.

The plurality of channels used in the invention, according to a preferred embodiment, are positioned at least substantially parallel. In their parallel positioning the axis of the channels preferably is at least substantially parallel with the blow direction. As the skilled person will understand this improves the flow of the forced gas flow through the channels.

For the channels used, according to some embodiments, the relation between the length (L) of the channel and the hydraulic diameter $D_H$ of the inlet or outlet, preferably the hydraulic diameter $D_H$ of the outlet, is such that $0.01 \leq D_H/L \leq 10$, wherein $D_H = 4 A/P$, (A) being the area of the of the inlet or respectively the outlet available for gas flow and (P) being the so called "wetted" perimeter or contact perimeter of the outlet or respectively the inlet. The contact perimeter (P) is the perimeter of the inlet, respectively the outlet that is in contact with the gas flow. As such (P) may be expressed as follows:

$$P = \sum_{i=0}^{\infty} li$$

wherein $(l_i)$ is the length of each surface in contact with the gas flow. According to some embodiments (P) corresponds to the circumference of the inlet or outlet.

The length (L) of the channel according to some embodiments is as defined above, i.e. the length of the centre line of the channel between the centre point of the inlet and the centre point of the outlet. The relation $D_H/L$ according to certain embodiments may have a value from 0.01 to 10, such as 0.05-8, such as 0.07-6, such as 0.07-4, such as 0.07-2, such as 0.07-1, such as 0.07-0.8, such as 0.1-0.4. For clarity, the stated endpoints of the ranges are within the values envisaged for the present invention.

According to some embodiments the hydraulic diameter $D_H$ of the outlet is similar or identical to the hydraulic diameter $D_H$ of the inlet (and vice versa). According to certain embodiments it is further preferred that for selected channels, the hydraulic diameter $D_H$ of the cross section of their body is identical to the hydraulic diameter $D_H$ of the outlet. It is further preferred in such cases that over a length of 0.3 L-1 L, such as 0.5-1 L, preferably 0.8 L-1 L, (L) being the length of the channel, the hydraulic diameter of the cross section of the channel body is identical to the hydraulic diameter $D_H$ of the outlet. The part of the channel having an identical $D_H$ for its cross section as the outlet, preferably is adjoining the outlet.

The length (L) of the channels according to some embodiments may be between 1 and 100 cm, such as 5-80 cm, such as 6-70 cm, such as 7-60 cm, such as 8-50 cm, such as 9-40 cm, such as 10-30 cm, such as 10-20 cm, such as 10-15 cm. Combinations of $D_H/L$ values with the length (L) of the channels envisaged by the present invention are presented in FIG. 8.

The area (A) of the outlet may have a value of between 10 mm² and 40.000 mm², such as 400-6.400 mm², such as 400-4.900 mm², such as 400-3.600 mm², such as 900-3.600 mm², such as 900-2.500 mm², such as 900-2.000 mm², such as 1.200-1.800 mm². For clarity, the stated endpoints of the ranges are within the values envisaged for the present invention. It should be noted that the area of the inlet may differ from the area of the outlet. As such the area of the inlet may also be outside the ranges specified for the area of the outlet. However, according to certain preferred embodiments, the area of the inlet is within the ranges specified above for the outlet. Channels having an inlet and an outlet having a similar or the same area are preferred. Combinations of the $D_H/L$ values with the area (A) of the channels envisaged by the present invention are presented in FIG. 9.

The selection of suitable materials for forming the channels is within the ambit of the skilled person. Any material suitable for guiding the forced gas flow may be selected. For example, metals, plastics or composite materials may be used. The use of metals, such as metals selected from steel or aluminium, according to certain embodiments is preferred. According to other embodiments the selection of plastics is preferred.

The outlets of the plurality of channels in the invention are designed to direct the gas outflows in the same direction. The term "designed" and equivalent terms when referring to outlets (and also to inlets) of the channels may include the shape, dimension and arrangement, such as the arrangement relative to the forced gas flow and/or the arrangement relative to other channels, of the channel. "In the same direction" means that the gas outflows substantially have an identical direction and thus that the direction of the gas outflows are substantially parallel. When considering the direction of a gas flow in the context of this invention, the direction of the core of the gas flow is considered. In certain embodiments the direction of the core of the gas flow is the direction of the centre line of the gas flow. Directing the outflows of gas going through the channels in the same direction may be accomplished by arranging the outlets of the plurality of channels such that the planes of the outlets are substantially parallel. For this the outlets may be arranged in a grid-like arrangement. In the context of the present invention, the gas outflows are considered directed in the same direction in case the core of the gas flows have the same direction. In case the core of the gas flows have the same direction such gas flows can be considered to be substantially parallel. Within this description and the attached claims the term "substantially" means "with little or no deviation". "Substantially parallel" within this description and claims of the invention thus should be understood to mean, "in essence parallel", meaning with little or no deviation from parallel. "At least substantially parallel" means substantially parallel or parallel. In view of the fact that in practice there is always some deviation from perfect parallel and some degree of error tolerance is always acceptable, it should be understood that where in connection to this invention reference is made to parallel, this includes parallel and substantially parallel. According to certain embodiments (substantially) parallel is (substantially) parallel in all directions.

According to certain embodiments used outlets have a stretched rectangular shape. These may be positioned such that the longest axis has a horizontal position or a vertical position. The selection of outlets having a stretched rectangular shape having a vertical longest axis is preferred over outlets have a stretched rectangular shape having a horizontal longest axis.

The outlets of the channels according to some embodiments are arranged such that the outlet of at least one other channel is positioned in its proximity. According to the invention an outlet is considered to be in the proximity of another, in case the distance (d) between their external circumferences is such that d≤a, preferably d≤0.5a, more preferably d≤0.2a, such as d≤0.1a, where (a) is the diameter of the outlet under consideration having the smallest diameter.

According to some embodiments, it is preferred that at least a part of the plurality of channels are adjoining. The term adjoining should be understood to mean that the channels abut. The channels may be (at least partially) adjoining or abutting in that their bodies (at least partially) contact. It is preferred that at least partially adjoining channels adjoin at the outlets. At least partially within this description of the invention includes the terms substantially and completely. According to certain embodiments channels adjoin over the full length of their channel bodies. Channels may have shared walls such as for example is the case in a grid, wherein for example the opposite side of a left wall of a first channel is the right wall of a second channel and vice versa. According to certain preferred embodiments substantially all or all of the plurality of channels are positioned in an (at least partially) adjoining configuration. The positioning of the channels in an adjoining configuration reduces the fraction gas flow outside the channels. This may provide a more uniform flow pattern in the forced gas flow when it exits the plurality of channels.

The skilled person will understand that the kinetic energy and/or momentum carried by the forced gas flow is a factor that is decisive for the potential of the forced gas flow to carry along particles. Therefore, according to the invention, at least part of the forced gas flow is directed through the channels. This is achieved by designing the inlets such that at least a part of the forced gas flow flows through the channels. In general the inlets will have a shape, dimension and arrangement to allow a gas flow to enter the channels. As the skilled person will understand, this means that the inlets will have a shape, dimension and arrangement to allow a gas flow to enter and flow though the hollow body of the channels. This may be accomplished by arranging the inlets of the channels such that the planes of the inlets are substantially parallel. For this the inlets may for example be arranged in a grid-like arrangement. The skilled person will understand that the total area of the inlets, the area of the individual inlets and the position of the inlets relative to the gas displacer are factors that influence the fraction of the forced gas flow that will flow through the channels.

According to certain embodiments, the fraction of the gas volume flow rate (volume of gas per unit time for example expressed in $m^3/s$) of the forced gas flow flowing through the channels is over 50% (>50%). The skilled person will be able to determine the free gas volume flow rate generated by the gas displacer (when not arranged with the channels in the gas flow). The skilled person will also be able to determine the gas volume flow rate after the forced gas flow has passed through the arrangement of channels. On the basis of this the skilled person will be able to determine the fraction of the gas volume flow rate of the forced gas flow flowing through the channels by dividing these values and optionally converting the fraction to a percentage. The term "over 50%" in connection to this invention, whenever used, includes 51%-100%, such as 55%-100%, such as 60%-100%, such as 70%-100%, such as 75%-100%, such as 80%-100%, such as 85%-100%, such as 90%-100%, such as 95%-100%, such as 96%-100%, such as 97%-100%, such as 98%-100%, such as 99%-100%.

The positioning and/or design of the inlets of the channels according to certain embodiments is such, that this facilitates the directing of the major part of the forced gas flow through the channels. For this, according to certain embodiments, it is preferred that the positioning of the inlets of the channels relative to each other is such that they form a condensed stacking with little or no space left in between the inlets. This may be achieved by using a grid like configuration. The shape of the inlets in such a grid may be a rectangular shape, such as a square shape, or may be a different shape, such as a triangular, hexagonal or pentagonal shape. When a grid is used, the shape and size of selected inlets need not be uniform and may differ. In case inlets having a circular shape are selected, these may be positioned in a honey comb-like configuration or pattern. When using grid-like or honey comb-like configurations it is preferred that the thickness of the walls of the bodies of the channels are minimized, at least at the position of the inlet. This minimizes obstructions for the forced gas flow and may reduce pressure and/or energy losses in the forced gas flow. The use of steel plates, such as stainless steel plates, is preferred in connection to this in view of the high structural integrity at low thickness.

In the invention the particulate material is directed from the number of exits in the forced gas flow after the forced gas flow has passed through the channels. This is preferably done such that for the number of exits the horizontal distance (X) to the outlets of the channels is between 0 to 100 cm. The horizontal distance (X) being the horizontal distance between an imaginary vertical line through the outlets of the channels to an imaginary vertical line through the considered exit. The phrase "0 to 100 cm" in connection to this invention includes 0-99 cm, such as 0-90 cm, such as 0-85 cm, such as 10-85 cm, such as 10-80 cm, such as 10-75 cm, such as 10-70 cm, such as 10-65 cm, such as 10-50 cm, such as 15-50 cm, such as 20-50 cm, such as 30-40 cm. In connection to the position of the exits in the horizontal plane, the skilled person will understand that it is preferred to position the number of exits in or substantially in (near) the centre of the forced gas flow. In case a rotor or propeller is used as a gas displaces, the number of exits in their horizontal plane are preferably positioned in or near a vertical plane through the axis of the rotor or propeller.

According to some embodiments, the distance of the position of the exits from the vertical plane through the axis of the rotor or propeller is between 0 cm and 0.5 R, wherein R is the radius of the circle the rotor (or propeller) blades describe in their circular movement. Concerning the position of the exits in the vertical plane, it is preferred to position the exits above the forced gas flow or in the upper parts of the forced gas flow, such that the particles may move through the forced gas flow under the influence of gravity. This is preferably done such that the vertical distance (Y) from the exits to the outlets of the channels is between 0 to 100 cm, preferably 0-50 cm, such as 5-20 cm. The vertical distance (Y) being the vertical distance between an imaginary horizontal line through the highest positioned outlet of the channels to an imaginary horizontal line through the considered exit.

In the method according to the invention the forced gas flow preferably is generated or directed above the target area wherein the particles are to be distributed. The target area may be a crop or any other area where the presence of the particles of the particulate material may be required. Alternative, in case the particulate material comprises beneficial arthropods, according to certain embodiments, the target areas where the beneficial arthropods may be distributed are stables for poultry or other farm animals. In such stables selected beneficial arthropods may be used to control pest arthropods that parasitize on the farm animals, such as the poultry red mite which parasitizes on amongst others chickens. It is within the ambit of the skilled person to select suitable beneficial arthropods that may predate on such pest arthropods. For example, as is known, predatory mites selected from the genera *Hypoaspis*, for example *Hypoaspis aculeifer*; *Cheyletus*, for example *Cheyletus eruditus*; *Androlealaps*, for example *Androlealaps casalis*; or *Macrocheles*, for example *Macrochelus robustulus* may be used as predators of poultry red mite (see for example WO2010/079353).

Generating or directing the forced gas flow above the target area may be achieved by placing the gas displacer above the target area and/or by placing an exhaust of a duct system directing the forced gas flow from the gas displacer above the target area. While simultaneously conveying the forced gas flow through the channels and introducing the particles in the forced gas flow, the gas displacer may be moved above the target area, preferably in a straight movement. Moving the gas displacer preferably takes place in a substantially horizontal plane. In addition to this, moving the gas displacer preferably is such that the direction of movement has a directional component perpendicular to the direction of the gas displacement. Most preferably the forced gas flow is moved in a substantially horizontal plane, substantially perpendicular to the direction of the forced gas flow.

A direction having a directional component perpendicular to the direction of the forced gas flow is, such as the skilled person will understand, a direction deviating from the direction of the forced gas flow or deviating from the opposite direction. Or in other words, the direction having a directional component perpendicular to the direction of the forced gas flow makes an angle with the direction of the forced gas flow larger than 0° and smaller than 180°.

Moving the gas displacer may be achieved by moving the gas displacer itself and/or an exhaust of a duct system directing the forced gas flow from the gas displacer. This may be achieved automatically, for instance by using an automated transport system. Examples of such transport systems are rolling and hanging transport systems, for instance a monorail system used for spraying robots known in the greenhouse agriculture. In a preferred embodiment of the method according to the invention the gas displacer is moved by means of a spraying robot.

In a preferred embodiment the forced gas flow is generated such that the particles are blown over a maximal distance in the axial direction (in the blow direction) of 0.5-8 metres, preferably about 3-6 metres, more preferably about 4-6 metres, even more preferably about 4-5 metres. This maximal blowing distance is the maximal distance where particles land in the distribution pattern of the particles. The indicated maximal blowing distances are well suited for use within (greenhouse) agriculture. According to certain embodiments, these maximal distances may be achieved with a forced gas flow having a gas velocity at a horizontal distance of 30 cm from the gas displacer of 0-20 m/s. Preferably this gas velocity is 5-15 m/s, most preferably 9-13 m/s. According to certain embodiments, these gas velocities are generated in a forced gas flow having a diameter of 10-100 cm, preferably 20-60 cm, such as 20-30 cm. The diameter of the forced gas flow referred to is at its point of expansion, where the forced gas flow expands freely.

When using a forced gas flow that is strong enough to achieve the above indicated maximal blowing distances, the chance is big that in the first metres, after the point of introduction of particles in the forced gas flow no particles will be distributed. This may negatively influence the distribution of the particles. Therefore, according to a further preferred embodiment of the method a fraction of the particles is blown by a gas flow, the counter gas flow, in a direction having a directional component perpendicular to the direction of the forced gas flow. Preferably the fraction of particles is blown by the counter gas flow in a direction, also having a directional component opposite to the direction of the forced gas flow. This causes that this fraction of the particles will not end up in the forced gas flow. Instead, this fraction is blown besides the forced gas flow and will fall at a distance, where otherwise no particles would land because of the high power of the gas flow. In this embodiment it is preferable that the particles are introduced in the forced gas flow at a certain distance from the generation of the forced gas flow. Preferably the fraction of particles is blown by the counter gas flow before the particles are introduced into the forced gas flow.

As the skilled person will understand, a direction having a directional component opposite to the direction of the forced gas flow makes an angle with the direction of the forced gas flow. Relative to the direction of the forced gas flow the angle of the counter gas flow thus may be between 1° and 90°, preferably between 10° and 80°, such as between 15° and 55°, preferably 25-45°. Preferably about 10% to 30%, more preferably 15%-25% of the particles is blown by the counter gas flow.

The counter gas flow may for example be generated by a means that is also suitable for generating the forced gas flow. It should be understood that the means for generating the counter gas flow may have smaller dimensions than the means for generating the forced gas flow. The counter gas flow for example is suitable to blow the particles over a horizontal distance of maximal 0.3-1.5 metres, more preferably 0.5-1 metre, most preferably 0.8-1 metre.

In an alternative embodiment for generating the counter gas flow a part of the forced gas flow may be direct through a duct. The inlet of the duct hereby is positioned such that the forced gas flow may enter it. The outlet of the duct is positioned such that the gas flow exiting from it may function as counter gas flow. According to certain embodiments the inlet of the duct for directing the counter gas flow is positioned opposite an outlet of one of the channels. This ensures a good entry of the forced gas flow into the duct. According to a different embodiment the inlet of the duct for directing the counter gas flow is connected to the outlet of one of the channels. This ensures a good entry of the forced gas flow into the duct. According to certain embodiments the entry of the forced gas flow into the duct for directing the counter gas flow is regulated by an adjustable gas flow restrictor. The adjustable gas flow restrictor may be positioned at the inlet of the gas return duct. In certain embodiments the adjustable gas flow restrictor may alternatively be positioned in a connection of the inlet of the duct for directing the counter gas flow with the outlet of one of the channels. Selection of suitable adjustable gas flow restrictors is within the ambit of the skilled person. These may for example be selected from valves, slides, gates or doors.

In a further preferred embodiment of the method multiple forced gas flows are generated in differing directions. These two differing directions preferably are perpendicular to each other. As is clear from this description, according to other preferred embodiments, the differing directions include opposite directions. In all directions of the forced gas flow the method may be performed in accordance to one of the above mentioned embodiments.

In a further preferred embodiment of the invention a nebulised fluid is directed into the forced gas flow. Particles such as beneficial arthropods may comprise allergens. Also beneficial arthropods such as predatory mites may be combined with other mites or other arthropods, for example such as in the mite composition described in WO 2006/057552. These added mites, or other arthropods may also be a source of allergens. Due to blowing of the particles of particulate material comprising arthropods their allergens may be spread. This may cause problems to persons who are (over) sensitive to these allergens. It has been shown that nebulising a fluid in the forced gas flow reduces problems in relation to spreading of allergens. It is believed that the allergens at least partially are captured in the nebulised fluid, and thereby settle faster. Means for nebulisation of fluids are known to the skilled person.

The nebulised fluid may suitably be selected from water and solutions comprising water. For certain applications, such as for the distribution of certain life stages of certain arthropods, such as pupae or eggs, it is preferred to add an adhesive to the nebulisation fluid. Hereby these life stages may stick to various substrates such as plant parts. A suitable adhesive is for example carboxymethylcellulose.

The method according to the invention is applicable broadly for example in agriculture in general and (greenhouse) horticulture in general. Of particular interest is that the method according to the invention makes it possible to distribute particulate materials comprising beneficial arthropods efficiently in crop production systems. This is especially of interest where the crops are grown in beds having little or no access, such as used in the production of *Rosa* and *Chysanthemum* species. However, as the skilled person will understand the potential utility of the invention is much broader.

The invention further relates to a device suitable for performing the above described method. The device comprises a reservoir suitable for holding a particulate material comprising particles that may be distributed by blowing. The reservoir is provided with a number of exits for the particles.

The device further comprises a gas displacer suitable for generating a forced gas flow, which forced gas flow is suitable for blowing the particles that may be blown. The function, operation and suitable means that may serve as gas displacer are discussed in relation to the method according to the invention.

Furthermore, the device comprises means to direct the particles from the reservoir via the exits in the forced gas flow. The function, operation and suitable means that may be used to direct the particles from the reservoir via the exits in the forced gas flow, are discussed in relation to the method according to the invention.

The device is characterised in that the device comprises a plurality of channels, each channel comprising an inlet, an outlet and a hollow body connecting the inlet and outlet, wherein the inlets are designed such that at least a part of the forced gas flow, when generated, flows through the channels and the outlets are designed to direct the gas outflows in the same direction and the means for directing the particles from the exits in the forced gas flow are designed to direct the particles in the forced gas flow after the forced gas flow has passed through the channels. The function, operation and further features and parameters relevant for the design of the channels are discussed above in connection to the method of the invention.

In a preferred embodiment, the device according to the invention comprises means to actuate the device. The device herein may be actuated by making use of actuation means which are part of the device, or alternatively the device may be loaded on a different device having actuation means. In both alternatives it is possible to actuate the device over the ground or hanging on a transport system. These transport means in a different preferred embodiment are suitable to actuate the device along a rail system, having a number of rails, such as a monorail. Hereby the device according to the invention is actuated comparable to a spraying robot, used in greenhouse horticulture, for example for the production of *chrysanthemum* or *Rosa* species. According to a further preferred embodiment the actuation means are suitable to actuate the device in a direction having a directional component perpendicular to the direction of the forced gas flow.

The device may comprise a plurality, for example two, gas displacers, positioned such that they may generate the forced gas flows in different directions, preferably in opposite directions. According to certain embodiments the device further comprises a container for a fluid and means to nebulise the fluid, which means for nebulising the fluid are suitable to introduce the nebulised fluid in the forced gas flow.

A further aspect of the invention relates to the use of the particle distribution device according to the invention in the distribution of a particulate material in a target area, such as a crop. The features relevant for this aspect of the invention will be clear for the skilled person in view of the description of the method of the invention and of the device for performing the method.

As is clear from the above description of the invention, an important part of the invention is a gas flow modification device comprising a plurality of channels, each channel comprising an inlet, an outlet and a hollow body connecting the inlet and outlet, wherein the inlets are designed to allow a gas flow to enter the channels, such that the gas flow is able to pass through the channels, and the outlets are designed to direct the outflows of gas going through the channels in the same direction, wherein said channels are arranged together as a unit. The gas flow modification device is a further aspect of the invention. Such a gas flow modification device according to certain embodiments may further comprise a number of fixing elements connected to the unit of channels, said fixing elements being suitable for fixing the unit of channels to a solid support.

The inlets of the channels of the gas flow modification device may be designed as is disclosed for the method and the particle distribution device of the invention. In general the inlets will have a shape, dimension and arrangement to allow a gas flow to enter the channels. As the skilled person will understand, this means that the inlets will have a shape, dimension and arrangement to allow a gas flow to enter and flow though the hollow body of the channels. This may be accomplished by arranging the inlets of the channels such that the planes of the inlets are substantially parallel. For this the inlets may for example be arranged in a grid-like arrangement.

The outlets of the channels of the gas flow modification device are designed to direct the outflows of gas going through the channels in the same direction. In the same direction meaning that the gas outflows substantially have an identical direction and thus that the direction of the gas outflows are substantially parallel. When considering the direction of a gas flow in the context of this invention, the direction of the core of the gas flow is considered. In certain embodiments the direction of the core of the gas flow is the direction of the centre line of the gas flow. Directing the outflows of gas going through the channels in the same direction may be accomplished by arranging the outlets of the plurality of channels such that the planes of the outlets are substantially parallel. For this the outlets may be arranged in a grid-like arrangement.

When both the inlets and the outlets of channels are arranged in a grid like arrangement, it is preferred to arrange the bodies of the channels such that they abut.

In the gas flow modification device, the channels are arranged together as a unit. This may be done by interconnecting the bodies of the channels. Alternatively this may be done by enclosing the plurality of channels in a fitting enclosure, preferably a tightly fitting enclosure, such as a casing or a housing or formed by a number of straps. In addition the channels may have shared walls such as for example is the case in a grid or a grid-like structure, wherein for example the opposite side of a left wall of a first channel is the right wall of a second channel and vice versa.

The gas flow modification device according to certain embodiments may further comprise a number of fixing elements connected to the unit of channels. The terms “fixing element” and “element for fixing” are equivalent in the context of the present invention. Fixing elements may be anything suitable for fixing the unit of channels relative to a solid support. The term fixing in the context of the present inventions should be understood to include to stably position, to attach, to connect, to fasten. Fixing elements thus include elements for attaching, elements for connecting, fastening means or elements for fastening. Fixing elements may include elements that are designed and/or configured to provide fixing in cooperation or jointly with other elements, such as is the case for a bore and a fitting screw, a bore and a fitting bold etcetera. According to some embodiments the number of fixing elements connected to the unit of channels comprise a number of, such as two, outwardly protruding flanges comprising a flat surface comprising a bore. As the skilled person will understand the flanges can cooperate with screws or bolds to fix the gas flow modification unit to a solid support.

In the gas flow modification device of the invention the inlets of the channels preferably are arranged to cover a circular area. This aids in collecting the gas flow from a rotating propeller or rotor. According to a further preferred embodiment the inlets of the channels are arranged to cover a circular area having a diameter of 10-100 cm, preferably 20-80 cm, such as 20-30 cm.

The various other technical features of this aspect of the invention, will be clear for the skilled person in view of the above detailed description of the method of the invention and the particle distribution device of the invention.

Still a further aspect of the invention relates to the use of the gas flow modification device of the invention for modifying a particle distribution device comprising a gas displacer for generating a forced gas flow. In the use of the gas flow modification device, the particle distribution device is modified in that its particle distribution is changed, in particular improved. More in particular the particle distribution in the axial direction (in the blow direction) is improved. The skilled person will understand that reference is made to the particle distribution by the particle distribution device when in function or when activated. The effect is accomplished by a modification of the forced gas flow generated by the gas displacer. Again, the forced gas flow generated by the gas displacer when in function or when activated is modified.

The particle distribution device according to certain embodiments may be a known particle distribution devices, such as an arthropods distribution device of the type disclosed in WO20071136246 (the embodiments related to the device of FIGS. 2-4). The gas flow modification device thus is suitable for modifying a device for distributing particulate material comprising particles, said device comprising a reservoir suitable for holding the particles, which reservoir is provided with a number of exits for the particles, a gas displacer suitable for generating a forced gas flow in a blow direction, which forced gas flow is suitable to carry along the particles in the blow direction, and means for directing the particles from the reservoir via the exits in the forced gas flow. In the use, the particle distribution device is modified by fixing the airflow modification device relative to the gas displacer and the means for directing the particles from the exits in the forced gas flow such that the forced gas flow, when generated, enters the inlets, flows through the channels and exits the outlets, while the means for directing the particles from the exits in the forced gas flow are in a position to direct the particles in the forced gas flow after the forced gas flow has passed through the channels.

The terms fixing will be clear for the skilled person, in particular in connection to the above clarification of the term “fixing means”.

According to certain embodiments, the gas displacer of the particle distribution device is a propeller or rotor.

The features relevant for this aspect of the invention will be clear for the skilled person in view of the description of the method of the invention and of the device for performing the method.

Still a further aspect of the invention relates to a kit of parts comprising:
(i) a gas flow modification device comprising a plurality of channels, each channel comprising an inlet, an outlet and a hollow body connecting the inlet and outlet, wherein the inlets are designed to allow a gas flow to enter the channels, such that the gas flow is able to pass through the channels, and the outlets are designed to direct the outflows of gas going through the channels in the same direction;
(ii) a device for distributing particulate material comprises a reservoir suitable for holding the particles, which reservoir is provided with a number of exits for the particles, a gas displacer suitable for generating a forced gas flow in a blow direction, which forced gas flow is suitable to carry along the particles in the blow direction, and means for directing the particles from the reservoir via the exits in the forced gas flow.

In view of the fact that a gas flow modification device may be easily assembled and/or disassembled form a device for the distribution of a particulate material comprising particles, it is clear that the gas flow modification device alone and the combination of the devices in unassembled form is of commercial value.

The kit of parts may further optionally comprise an information carrier comprising a manual with instructions for connecting the gas flow modification device to the particle distribution device. The instructions in the manual may be presented in text and/or in pictograms. The information carrier may be any suitable information carrier, such as an information carrier carrying printed information or an information carrier containing an electronic file comprising the manual in electronic form. An information carrier containing an electronic file may be a physical information carrier, such as a ROM or RAM memory module, an optical memory disk such as a CDROM disk, DVD disk or Blue Ray disk, or may be an electronic signal transferring electronic information, for example via the internet.

The different aspects of the invention will now be discussed with reference to the figures which relate to exemplary embodiments of the invention.

FIG. 1 shows an embodiment of a device 1 according to the invention. This device 1 is suitable for performing the method according to the invention. The device 1 comprises a house 2 wherein two separate rotors each driven by an electromotor 4 are installed in separate cylindrical rotor chambers. The rotors are not visible due to their position in the interior of the housing 1. Only one of the electromotors 4 is visible from its back end via the inlet opening 5 of its rotor chamber covered with safety bars. The other rotor and its electromotor are positioned in a rotor chamber positions behind an gas flow modification unit 6 fixed to the house 1. Fixing of the gas flow modification unit 6 to the house 1 is accomplished by bolds fixed in bores in fixing ear 7 and the housing 1. Only one fixing ear 7 is presented in FIG. 1, as the other is located on an opposite position on the cylindrical mantle 8 of the gas flow modification unit 6.

The gas flow modification unit 6 comprises within its cylindrical mantle 8 an arrangement of a plurality of parallel channels which have different shapes in cross section, as is visible from the shape of their outlets 9 (in FIG. 1 only some exemplary outlets have been provided with the reference number 9). Most of the channels have a rectangular cross section, giving the arrangement a grid-like appearance. The nine channels in the centre have a square shape. At the borders where the channels come close to or neighbour the cylindrical mantle 8, the cross sections have alternative shapes.

As is visible, the total area of the parallel channels completely covers the outlet openings of the rotor chambers. Thus the whole of the forced gas flow generated by the rotors is conveyed through the parallel channels.

Figure 2:
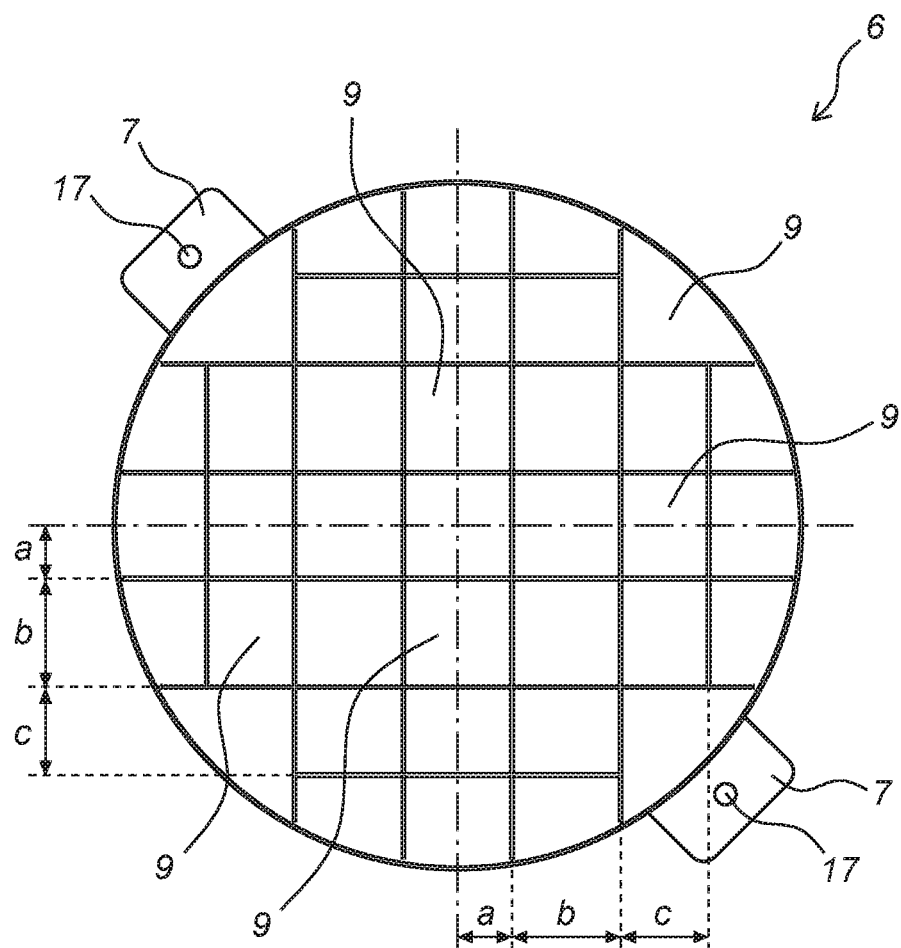

The device 1 further comprises reservoirs 10 for holding the particulate material comprising particles, in the exemplified case a composition comprising beneficial arthropods. These reservoirs 10 in this embodiment of the device according to the invention have the form of a cylinder with a bottom. In the mantle of the cylinder openings 11 are provided as a exit for the composition comprising beneficial arthropods. The bottom of the cylinder is connected with the driving shaft of an electromotor 12. Hereby in use the reservoir may be rotated around the axis of the cylinder mantle. During rotation of the reservoirs 10 the composition comprising beneficial arthropods will, under the influence of gravity, exit the openings 11 in a dosed fashion and will enter the forced gas flow exiting the outlets 9 of the gas flow modification unit. The openings 11 have a horizontal distance (x) to the outlets 9 of the gas flow modification unit. This horizontal distance (x) may differ for different openings 11.

The composition comprising beneficial arthropods will be carried along by the forced gas flow, moving under the influence of the combined forces of the forced gas flow and gravity. Hereby in general they will land at a certain distance of the device, with a certain distribution pattern. The force of the forced gas flow may cause that directly underneath the device and in the proximity thereof no or hardly any beneficial insects may land. To prevent this, the device in the presented embodiment comprises the optional means of the invention for generating a second gas flow, this second gas flow having a direction with a directional component, opposite to the direction of the forced gas flow and a directional component perpendicular to the direction of the forced gas flow. In the embodiment, as presented in FIG. 1, this is a tube 13 having an inlet 14 and an outlet 15. The inlet 14 of the tube 13 is positioned opposite of an outlet 9 of a parallel channel of the gas flow modification unit, such that a part of the forced gas flow enters it. This entering gas flow is directed through the inner space of the tube 13, and exits the outlet 15 positioned after a bend in the tube, such that the counter gas flow is created. Hereby a part of the arthropods that fall from openings 11 from the reservoir 10 during use are blown besides the forced gas flow. Due to this the arthropods will also, to a certain extent, land under the device and in the proximity thereof. Hereby a more equal distribution pattern of the beneficial arthropods is obtained.

For hanging the device on a spraying robot, the device is provided with hooks 16. This provides a solution for the labour intensive character of distribution of beneficial arthropods. As such, the device according to the invention may be actuated above the crop along a transport system of the spraying robot. Alternatively the device may have its own driving mechanism for transport along its own transport system, or the transport system of the spraying robot.

In the device in FIG. 1 the back side, which is not visible, is identical to the front side shown. Thus on the back side of the device 1 of FIG. 1, a similar gas flow modification device is fixed to the housing in front of the outlet of the rotor chamber for which the inlet opening 5 is shown on the right in FIG. 1.

FIG. 2 shows a front view of the gas flow modification unit 6 while not connected to the device as presented in FIG. 1. The differing shape of the cross sections of the channels is clearly visible in this view. For this particular embodiment the diameter of the cylinder mantle is 250 mm and the length of a, b and c indicated in FIG. 2 is respectively 20 mm, 40 mm and 32.5 mm. The length of the channels (and the cylinder mantle) is 120 mm. This results in $D_H/L$ values for the rectangular channels in the range of 0.25-0.35. The irregular shaped channels will have $D_H/L$ values in the same order. The gas flow modification device presented in FIG. 2 can be easily mounted over the rotor chamber of existing devices for distributing arthropods for example the Airobug™ device currently marketed by Koppert Biological systems to come to an arrangement as is presented in FIG. 1. For this the gas flow modification device is fixed to the housing of the arthropod distribution device via bolds placed in the bores 17 of fixing ears 7 and in the housing 2 of the device 1.

Figure 3:
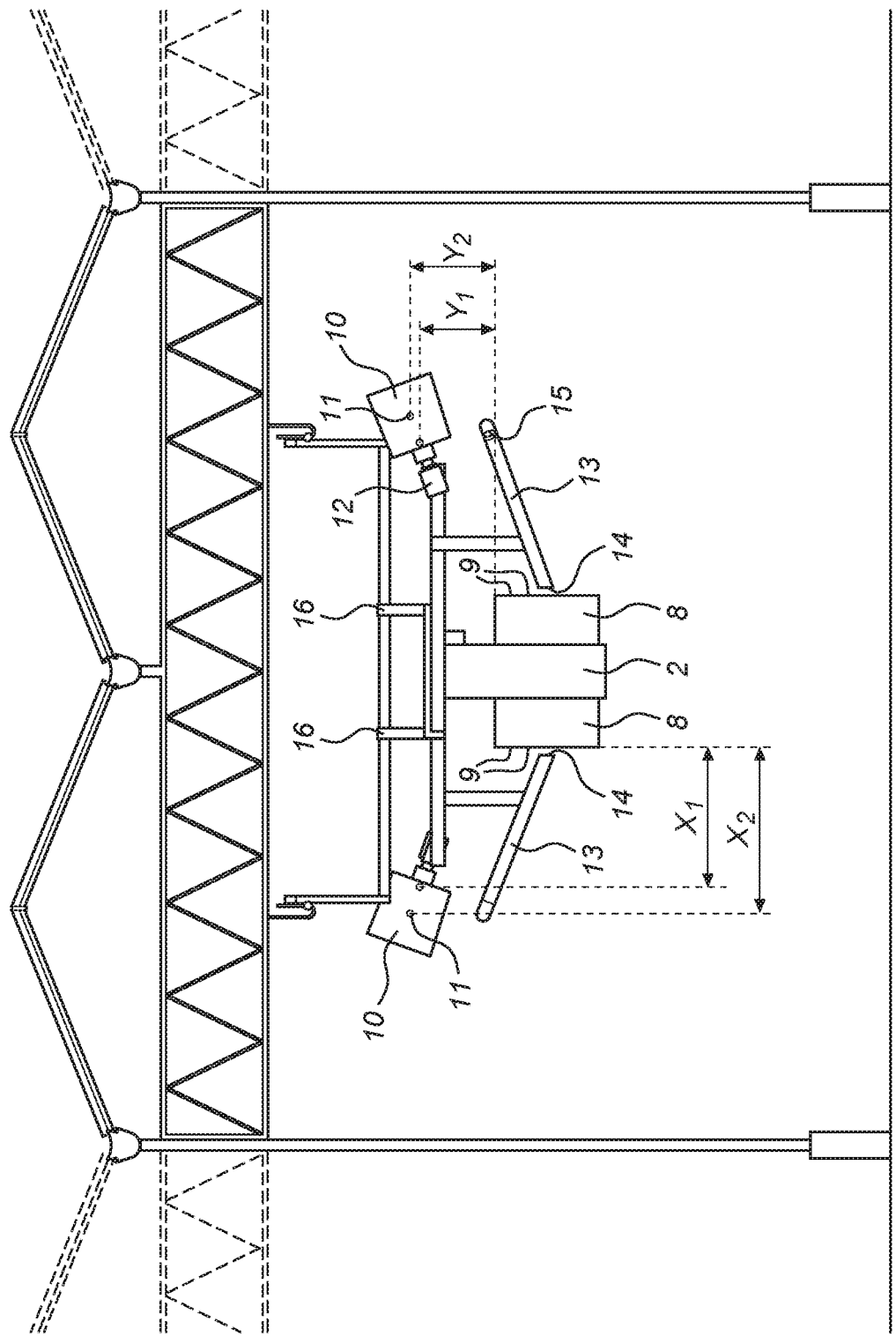

In FIG. 3 the device according to the invention in an embodiment is shown in a side view. The device in this embodiment is installed for use in a greenhouse. By using hooks lithe device is installed on the transport system 12 of the spraying robot. In this side view of FIG. 3, for the openings 11 shown on the left side, the horizontal distance x1 and x2 (from the openings 11 to the outlets 9 of the parallel channels are schematically indicated.

Figure 4:
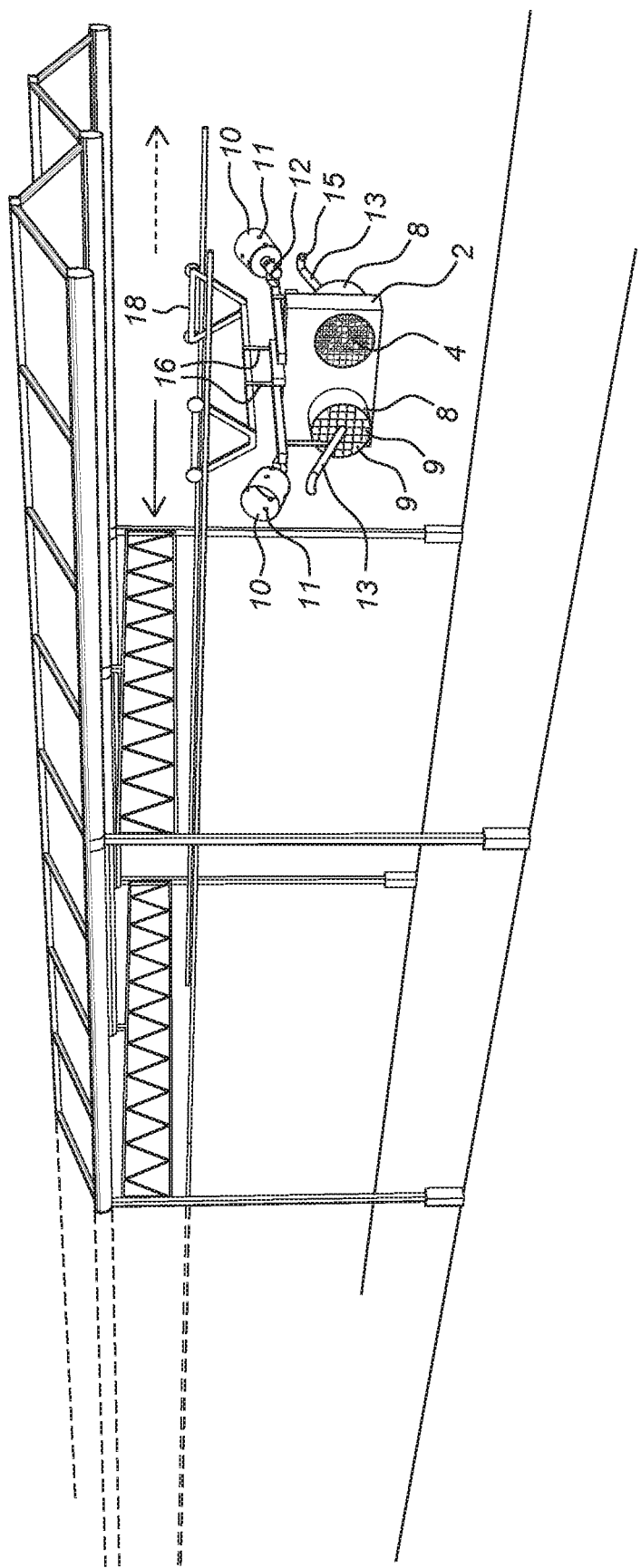
FIG. 4 shows a side view of an embodiment of the particle distribution device, as shown in FIG. 1, installed in a greenhouse.

In FIG. 4 the device according to the invention is shown in a different view, as it is installed in a greenhouse. In use the device will be moved along a transport system 18 in the direction of the arrow. In two opposite directions the forced gas flow is generated, perpendicular to the direction of movement. As such, the beneficial arthropods may be distributed efficiently in the crop, by moving the spraying robot and simultaneously blowing the beneficials sideward. After the distribution (dispersion) of the arthropods the device may be moved back to the starting position (in the direction of the broken arrow). Via a shunting device the device may thereafter be guided to a different track for distributing beneficial arthropods.

EXPERIMENTS

Experiment 1

Setup

In this experiment the effect of the use of the gas flow modification device on the distribution of particulate material was tested by comparison of the distribution of particulate material by a device according to WO2007/136246 (the embodiment of FIG. 2) not comprising the gas modification unit and a particle distribution device of the present invention containing the gas flow modification unit. The prior art device used was the Airobug™ device of Koppert Biological Systems (Berkel and Rodenrijs, The Netherlands) which is a device according to WO2007/136246. For obtaining a device of the present invention, a gas flow modification unit according to the present invention (as shown in the attached FIG. 2) was mounted to this Airobug™ device. In both the prior art setup and the set up according to the invention, the particle distribution device was used without the gas return duct (directing the counter gas flow; reference numeral 13 of the attached figures) mounted. Thus the prior art Airobug™ device was used in a somewhat modified form, as the model used in its marketed form normally is operated with the gas return duct. The air flow velocities measured directly in front of the outlet of the rotor chamber of the prior art device was between about 5 and 12 m/s (depending on the radial position). For the device of the invention, the air flow velocity measured directly in front of the outlets of the channels was between about 4 and 10 m/s (depending on the radial position). Air flow velocities were measured using a TESTO 410-2 gas flow meter. The diameter of the rotor chamber of the prior art device was 25 cm and the channels of the device of the invention had a total area corresponding with the area of the rotor chamber of the prior art device.

As a model for particulate materials the Spidex™ product of Koppert Biological Systems (Berkel and Rodenrijs, the Netherlands) was used. This product comprises the predatory mite *Phytoseiusleis persimilis* (a beneficial arthropod) combined with a saw dust carrier. For each run about 500 ml Spidex™ corresponding to about 10.000 predatory mite individuals was loaded into one of the holding containers of the particle distribution device positioned on a supporting table. The batch of the Spidex™ product used contained a (moistened) sawdust carrier having an average particle size of 0.75 mm and a density of about 170 g/l. The position of the exits of the container for both the measurement in the prior art setup and the setup according to the invention was about 160 cm above the floor surface.

On the floor in front of the table, a grid was marked out with tape. The grid was formed by 5 axial lines 6.5 m long and 14 lateral lines 1.2 m long, forming a grid having 52 equal rectangles of 0.3×0.5 m (area=0.15 m²). At the corner of each rectangle a coffee cup (area of opening=0.0125 m²) placed in a petri dish comprising water and soap was positioned. Thus in total 70 coffee cups were positioned on the corners of the grid with a total area of 7.8 m².

After loading of the Spidex™ product in the container of the particle distribution device, the device was activated until all of the particulate material was distributed. The forced gas flow generated distributed the particulate product over the area of the grid and also caused particles (mites and carrier) to land in the coffee cup. Due to the position of the coffee cup in the water/soap mixture, the very mobile *Phytoseiulus persimilis* mites were captured in and on the coffee cup. All *Phytoseiulus persimilis* individuals present in and on the individual coffee cups were carefully collected and their numbers were determined under a binocular.

Results

Visual inspections of the distribution patterns showed a differing distribution pattern between the two tested devices. The prior art device showed a concentration of distributed particles around 100-200 cm from the device. In addition, in the range >4 m, only little particulate material was distributed. Contrary to this, the device of the invention presented a more even distribution of the particulate material with no prominent concentration of distributed particles and a good coverage with particles in the >4 in area up to about 5.5 m.

Figure 5:
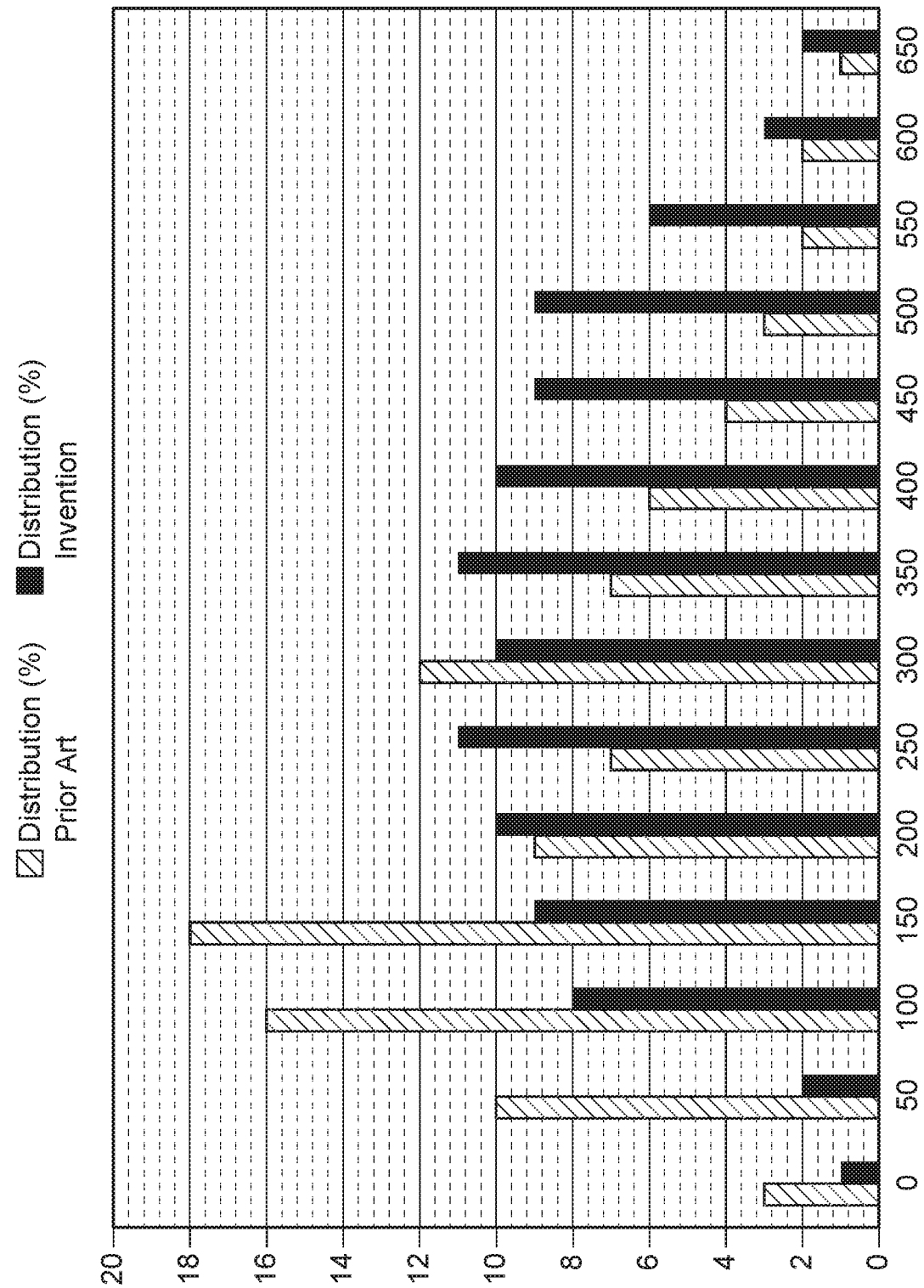
FIG. 5 shows a bar chart of the distribution (%) at different distances (cm) of the data presented in table I.

The results of the countings of the predatory mite individuals distributed with the prior art Airobug™ device (not containing the airflow modification unit) and with a particle device according to the present invention (containing the airflow modification unit), is presented in table I below. A graphical presentation of the (%) distribution at the measured distance (cm) is presented in FIG. 5.

TABLE I

COMPARISON OF DISTRIBUTION OF PRIOR ART AND INVENTION

| DISTANCE | Prior Art | | Invention | |
|---|---|---|---|---|
| (cm) | SUM | DISTRIBUTION | SUM | DISTRIBUTION |
| 0 | 10 | 3% | 2 | 1% |
| 50 | 34 | 10% | 4 | 2% |
| 100 | 53 | 16% | 16 | 8% |
| 150 | 62 | 18% | 18 | 9% |
| 200 | 30 | 9% | 22 | 10% |
| 250 | 23 | 7% | 24 | 11% |
| 300 | 41 | 12% | 22 | 10% |
| 350 | 25 | 7% | 23 | 11% |
| 400 | 21 | 6% | 21 | 10% |
| 450 | 14 | 4% | 18 | 9% |
| 500 | 9 | 3% | 18 | 9% |
| 550 | 7 | 2% | 12 | 6% |
| 600 | 8 | 2% | 6 | 3% |
| 650 | 3 | 1% | 4 | 2% |

The DISTANCE (cm) shows the distance from the device to the row of coffee cup which is counted. SUM is the sum of the number of mites which is counted in a particular row of coffee cups at the indicated distance. DISTRIBUTION shows the percentage of mites in every row (the total of the Sum of recovered mites is set to 100%). Invention Embodiment (−) GRD is the embodiment without gas return duct (GRD) tested in this experiment.

The results clearly show that the particulate material distribution device using the airflow modification unit has a more even distribution of the predatory mites than the prior art device. As expected, the difference of distribution of *Phytoseiulus persimilis* between the two tested devices corresponded to the visually observed differing distribution of the particulate carrier.

No dead or injured individuals of *Phytoseiulus persimilis* (a rather sensitive beneficial arthropod) were identified from the materials collected from the coffee cups. This clearly shows that the use of the gas flow generated by the gas modification unit can be safely used for distributing beneficial arthropods such as beneficial mites.

Experiment 2

Setup

In this experiment the distribution of particulate material by a different embodiment of the particle distribution device of the invention (with airflow modification unit) was compared with a prior art particle distribution device (without airflow modification unit). The prior art device used, again, was the Airobug™ device of Koppert Biological Systems Merkel and Rodenrijs, The Netherlands). For obtaining a device of the present invention, again, a gas flow modification unit according to the present invention (as shown in the attached FIG. 2) was mounted to this Airobug™ device. The difference between the devices of this experiment and those used in experiment 1 was that, in this experiment in both the prior art setup and the set up according to the invention, the particle distribution devices did have a gas return duct (reference numeral 13 of the attached figures) mounted. The gas flows measured with and without gas flow modification unit mounted were similar as those measured in experiment 1.

As a model for particulate materials (moistened) saw dust (particle size about 0.75 mm and density about 170 g/l) and moistened wheat bran (particle size about 2 mm and density about 225 g/l) were used. For each run about 1000 ml of the particulate material was loaded into one of the holding containers of the particle distribution device mounted on a stand. The position of the particle distribution device for the prior art setup and the setup according to the invention was such that the height of the exits of the container was about 200 cm. To aid in the visual inspection and photographic recording of the distribution pattern the floor in front of the device was covered with a dark plastic foil (improving the contracts) and paper sheets having printed numbers 1-6 were positioned at a distance in meters corresponding to the number printed on the sheets.

After loading of the particulate product in the container of the particle distribution device, the device was activated until all of the particulate material was distributed. The forced gas flow generated distributed the particulate product over the area in front of the device and the distribution pattern for the different device setups with the different particulate materials were visually inspected and digitally photographed.

Results

Figure 6:
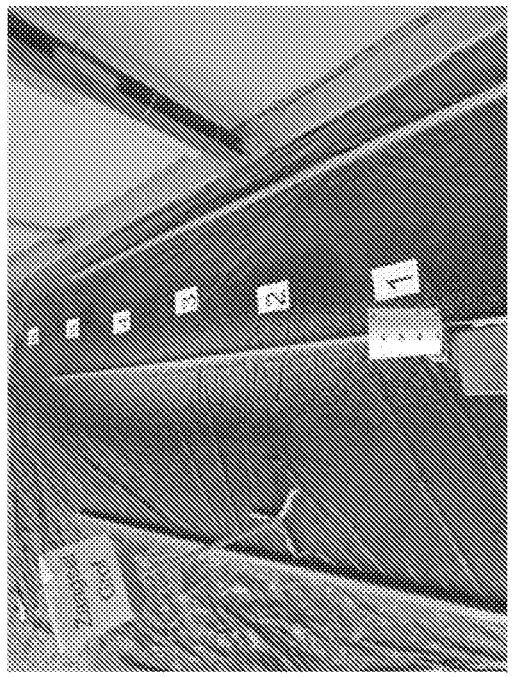
FIG. 6 shows different photographs (A-D) of the distribution of wheat bran and saw dust by a prior art device and a particle distribution device according to the invention.
Figure 6:
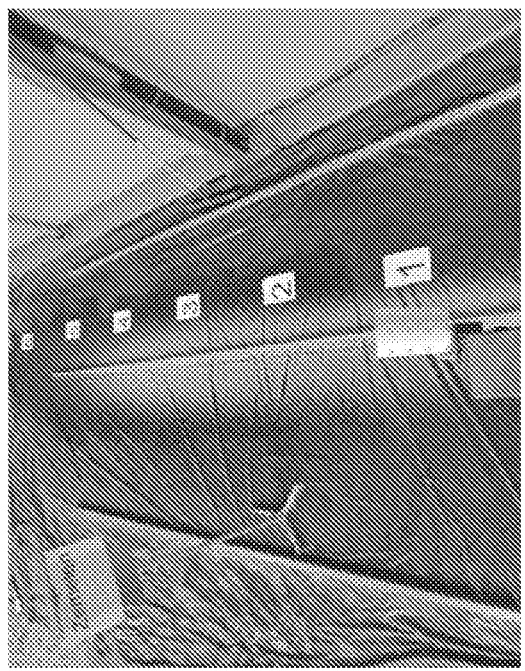
Figure 6:
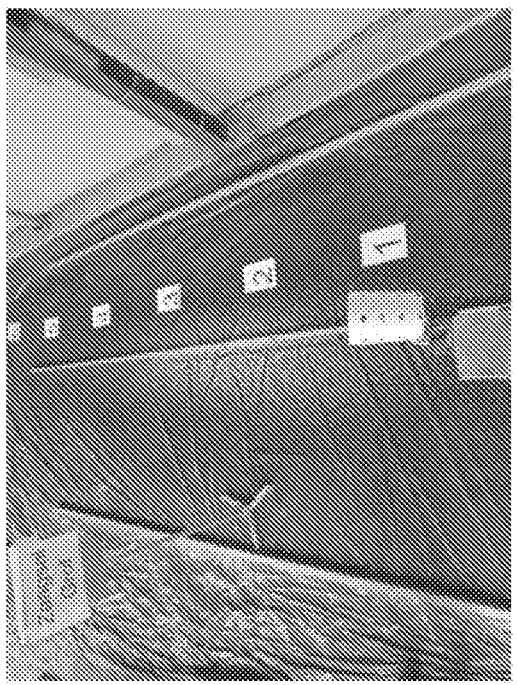
Figure 6:
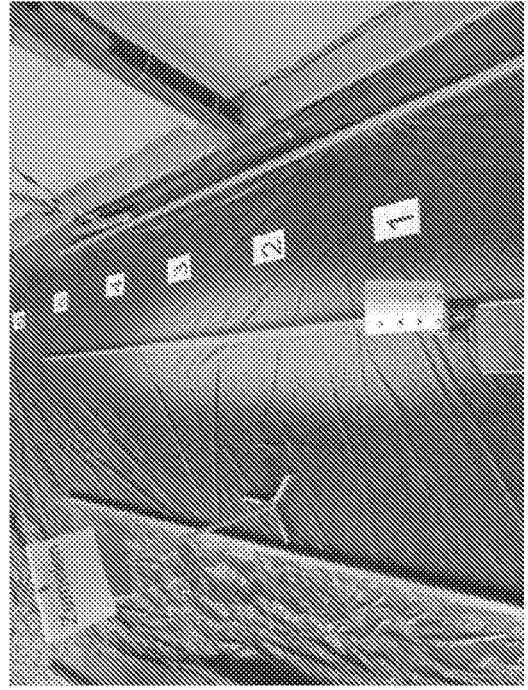

Pictures of the distribution pattern of the prior art device and the device according to the invention are presented in FIG. 6A-6D. FIGS. 6A and 6C show the distribution of saw dust by the prior art device and the device of the invention respectively. FIGS. 6B and 6D shows the distribution of wheat bran by the prior art device and the device of the invention respectively.

The distribution of both particulate materials by the prior art device was comparable. Similar to what was observed in experiment 1, the prior art device in this setup also deposited only little material beyond 4 m. Most material was deposited between 0.5-3.5.

Also for the device of the invention the distribution of both particulate materials was comparable. The distribution pattern of the device of the invention differed from the distribution by the prior art device. In particular the amount of material deposited in the 0-0.5 m range was higher for the device of the invention. Between 0 and 5.5 meters there was sufficient distribution of material. The distribution pattern in the lateral direction (perpendicular to the blow direction) for the device of the invention was smaller in comparison to that of the prior art device.

Overall the distribution of the device of the invention was better, in particular in view of the improved distribution at both the shorter and the longer distances. This provides a more stretched and more even distribution pattern.

For the distribution of particulate material comprising beneficial arthropods, such as predatory mites, it may be expected by the skilled person that the distribution pattern will follow the distribution pattern of the particulate materials as presented in this example, as saw dust and wheat bran are often used as carriers for beneficial arthropods and alternative carriers for beneficial arthropods, such as for example vermiculite, usually have comparable characteristics.

The invention claimed is:

1. A method for distributing particulate material comprising a composition comprising beneficial arthropods, said method comprising:
   (i) providing in a reservoir the composition comprising beneficial arthropods to be distributed in a target area, wherein the reservoir comprises a number of exits for the particles of the composition;
   (ii) providing a gas displacer suitable for generating in a blow direction a forced gas flow that can carry the particles of the composition;

(iii) generating with the gas displacer in the blow direction the forced gas flow that can carry the particles of the composition; and (iv) distributing the particles of the composition by introducing the particles of the composition from the exits in a distributing gas flow that carries the particles in the blow direction, wherein the distributing gas flow is formed from the forced gas flow;

wherein a plurality of channels is provided, each channel comprising an inlet, an outlet and an elongated hollow body connecting the inlet and outlet, said channels adjoining at least at the outlets, wherein the inlets are designed such that at least a part of the forced gas flow flows through the channels and the outlets are designed to direct the forced gas outflows in substantially the same direction, such that the forced gas outflows from the plurality of outlets and combines to form the distributing gas flow, and the particles of the composition are introduced from the exits of the reservoir in the distributing gas flow after the forced gas outflows have outflown from the plurality of outlets and have combined to form the distributing gas flow.

2. The method according to claim 1, wherein the channels are positioned in the forced gas flow in an at least substantially parallel position.

3. The method according to claim 1, wherein the gas displacer is moved above the target area in a direction having a directional component perpendicular to the direction of the gas flow.

4. The method according to claim 1, wherein the distributing gas flow has a power adjusted to blow the particles of the composition over an axial distance of at most about 0.5-8 meters.

5. The method according to claim 1, wherein a fraction of the particles of the composition is blown by a counter gas flow in a direction having a directional component perpendicular to the direction of the distributing gas flow, wherein the fraction of the particles of the composition is blown by the counter gas flow before introduction in the distributing gas flow.

6. The method according to claim 5, wherein the fraction of the particles of the composition is blown by the counter gas flow in a direction also having a directional component opposite to the direction of the distributing gas flow.

7. The method according to claim 1, wherein the distributing gas flow is generated above the target area and the particles of the composition are introduced in the forced gas flow above the target area.

8. The method according to claim 1, wherein the beneficial arthropods are beneficial mites.

9. The method according to claim 1, wherein the beneficial arthropods are predatory mites.

10. The method according to claim 1, wherein the beneficial arthropods are Astigmatid prey mites.

11. The method according to claim 1, wherein the beneficial arthropods are a combination of predatory mites and Astigmatid prey mites.

\* \* \* \* \*